(12) United States Patent
Wu et al.

(10) Patent No.: US 11,389,081 B2
(45) Date of Patent: Jul. 19, 2022

(54) NON-INVASIVE PHOTONIC SENSING FOR MONITORING DIABETES

(71) Applicant: AUSMED GLOBAL LTD, Hong Kong (CN)

(72) Inventors: Chujun Wu, Ultimo (AU); Xiaoke Yi, Sydney (AU)

(73) Assignee: AUSMED GLOBAL LTD., Hong Kong (CN)

( * ) Notice: Subject to any disclaimer, the term of this patent is extended or adjusted under 35 U.S.C. 154(b) by 276 days.

(21) Appl. No.: 16/348,065

(22) PCT Filed: Nov. 7, 2017

(86) PCT No.: PCT/AU2017/051224
§ 371 (c)(1),
(2) Date: May 7, 2019

(87) PCT Pub. No.: WO2018/081877
PCT Pub. Date: May 11, 2018

(65) Prior Publication Data
US 2019/0282124 A1    Sep. 19, 2019

(30) Foreign Application Priority Data
Nov. 7, 2016 (AU) ................................ 2016904530

(51) Int. Cl.
*A61B 5/083*    (2006.01)
*A61B 5/00*    (2006.01)
(Continued)

(52) U.S. Cl.
CPC ............ *A61B 5/083* (2013.01); *A61B 5/0008* (2013.01); *A61B 5/08* (2013.01); *A61B 5/082* (2013.01);
(Continued)

(58) Field of Classification Search
None
See application file for complete search history.

(56) References Cited

U.S. PATENT DOCUMENTS 6,468,222 B1 * 10/2002 Mault ................... A61B 5/0833
600/529
7,790,467 B1    9/2010 Massick
(Continued)

FOREIGN PATENT DOCUMENTS

JP        63-75561 A  *  4/1988
WO    WO-2005108968 A1 * 11/2005  ............. C12Q 1/006

OTHER PUBLICATIONS

Marasco, Martin, "Hydroxylamine hydrochloride for the quick estimation of acetone" Industrial & Engineering Chemistry, vol. 18, No. 7, published date Jul. 1, 1926, pp. 701-702. (Year: 1926).*

(Continued)

*Primary Examiner* — Michael R Bloch
(74) *Attorney, Agent, or Firm* — Moser Taboada

(57) ABSTRACT

The present disclosure relates to a device (100) for monitoring a biomarker in an exhaled breath, the device (100) utilising a combination of a sensing element (110) having a thermochemical reactant (120) that undergoes a thermochemical reaction with the biomarker and a thermal sensor (140) positioned to measure a rate of change in temperature caused by the thermochemical reaction. A user interface (170) is provided for indicating to a user an indicated measure of the biomarker in the exhaled breath, wherein the indicated measure of the biomarker in the exhaled breath is determined from the measured rate of change in temperature.

18 Claims, 11 Drawing Sheets

(51) Int. Cl.
*A61B 5/087* (2006.01)
*G01N 33/64* (2006.01)
*A61B 5/08* (2006.01)

(52) U.S. Cl.
CPC ............ *A61B 5/087* (2013.01); *A61B 5/7475* (2013.01); *G01N 33/64* (2013.01); *A61B 2560/0252* (2013.01); *A61B 2562/0276* (2013.01); *G01N 2800/042* (2013.01)

(56) References Cited

U.S. PATENT DOCUMENTS

| | | | |
|---|---|---|---|
| 8,932,525 B1 | 1/2015 | Ahmad et al. | |
| 2004/0236244 A1* | 11/2004 | Allen | ................. C12P 7/04 600/532 |
| 2006/0133960 A1* | 6/2006 | Ahmad | ................. A61B 5/083 422/83 |
| 2008/0004542 A1 | 1/2008 | Allen et al. | |
| 2008/0053194 A1 | 3/2008 | Ahmad | |
| 2008/0273572 A1 | 11/2008 | Lawrence et al. | |
| 2010/0282969 A1* | 11/2010 | Frank | ................. G01N 21/27 250/339.07 |
| 2016/0061793 A1 | 3/2016 | Hansmann et al. | |
| 2016/0242674 A1 | 8/2016 | Ahmad et al. | |
| 2017/0065208 A1* | 3/2017 | Furusaki | ............ G01N 27/4067 |

OTHER PUBLICATIONS

Machine translation of WO 2005108968A1, accessed Jun. 19, 2021 (Year: 2005).*

Marasco, Martin, "Hydroxylamine hydrochloride for the quick estimation of acetone" Industrial & Engineering Chemistry, vol. 18, No. 7, published date Jul. 1, 1926, pp. 701-702.

International Search Report for application No. PCT/AU2017/051224 dated Jan. 15, 2018.

* cited by examiner

NON-INVASIVE PHOTONIC SENSING FOR MONITORING DIABETES

CROSS-REFERENCE TO RELATED APPLICATIONS

The present application claims priority from Australian Provisional Patent Application No 2016904530 filed on 7 Nov. 2016, the content of which is incorporated herein by reference.

TECHNICAL FIELD

The present disclosure relates generally to a device for monitoring biomarkers in exhaled breath and, in particular, to a portable breath monitoring device for the diagnosis and monitoring of diseases and/or physiological processes occurring in a subject's body through the detection of biomarkers in the breath.

BACKGROUND

Exhaled human breath is made up of a wide variety of compounds. The presence of certain compounds and/or their quantity can be indicative of disease and/or physiological processes occurring in the body. For example, the detection and measurement of certain biomarkers in exhaled breath can assist in the diagnosis and/or monitoring of diseases such as diabetes, lung cancer, renal failure, liver disease and asthma in a non-invasive manner. In particular, measurements of the biomarker acetone in the breath can assist in the monitoring of diabetes.

Ketones are organic compounds containing a carbonyl group (=C=O) bonded to two hydrocarbon groups. Ketosis is a metabolic state in which the body burns fat for energy resulting in a release of the ketones acetone, acetoacetic acid and beta-hydroxy butyric acid into the bloodstream from the liver. In healthy subjects, increased levels of ketones can occur as a result of a period of fasting or being on a low-carbohydrate diet. In type 1 diabetes, however, the presence of high levels of ketones in the bloodstream is indicative of insufficient insulin.

When the body has insufficient insulin, it cannot process glucose from the blood into the body's cells to use as energy and will instead begin to burn fat. The liver converts fatty acids into ketones which are then released into the bloodstream for use as energy. In people that are insulin dependent, such as people with type 1 diabetes, high levels of ketones in the blood can result from taking too little insulin and this can lead to ketoacidosis, a serious short term complication which can result in coma or even death if it is not treated quickly.

Management of type 1 diabetes typically requires regularly monitoring blood glucose levels, which can be an invasive and painful procedure, particularly for diabetics who are required to undertake multiple blood tests throughout the day, and administering insulin injections. Ketone testing can be done via a blood test utilising modern blood glucose meters and specialised ketone testing strips, or through urine test strips. Although less invasive, testing urine for ketone levels can be inaccurate as the results are not real-time but rather indicative of a subject's ketone levels up to several hours prior.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

There is provided a device for monitoring a biomarker in an exhaled breath, the device comprising:

a sensing element comprising a thermochemical reactant that undergoes a thermochemical reaction with the biomarker;

a thermal sensor positioned to measure a rate of change in temperature caused by the thermochemical reaction; and a user interface for indicating to a user an indicated measure of the biomarker in the exhaled breath, wherein the indicated measure of the biomarker in the exhaled breath is determined from the measured rate of change in temperature.

The sensing element may further comprise a sensitivity booster in contact with the thermochemical reactant, wherein the sensitivity booster undergoes a thermochemical reaction with a product of the reaction between the thermochemical reactant and the biomarker. The sensitivity booster may be at least one layer on and/or under the thermochemical reactant and/or the sensitivity booster may be dispersed in the thermochemical reactant.

The thermal sensor may measure the rate of change in temperature directly or indirectly. In certain embodiments, the thermal sensor may be in contact with the sensing element. Alternatively, the thermal sensor may be spaced apart from the sensing element.

The sensing element may comprise a support element for supporting the thermochemical reactant. In some embodiments, the thermochemical reactant is coated on at least one surface of the support element. Alternatively, the thermochemical reactant is impregnated onto the support element. The shape of the support element is not particularly limited, for example the support element may substantially planar or substantially tube shaped.

The sensing element may be mounted in a housing, the housing comprising an inlet for receiving the exhaled breath. The housing may be formed of a thermally insulating material. The inlet may include a one-way valve, such as a check valve, to prevent gas flow from the device out through the inlet. The sensing element may be removably mounted in the housing such that the sensing element can be replaced after each use without the need to replace the other components of the device.

In order to determine the volume of exhaled breath being analysed, the device may be configured to receive a predetermined volume of the exhaled breath. In other embodiments, the determination of the volume of exhaled breath being analysed may be determined by a flow meter for measuring the flow rate of the exhaled breath into the device.

The biomarker may be any compound that may be expressed in a subject's exhaled breath, for example the biomarker may be selected from the group comprising ketones, volatile organic compounds (VOCs), hydrocarbons, ammonia, amines and sulphides. In particular, the biomarker may be acetone.

Where acetone is the biomarker, the thermochemical reactant is selected from the group comprising: hydroxylamine hydrochloride, o-benzylhydroxylamine-hydrochloride, hydrogen peroxide and chloroform. In one embodiment, the thermochemical reactant is hydroxylamine hydrochloride and the sensitivity booster is a metal such as aluminium.

In certain embodiments, the sensitivity of the device may be affected by the presence or lack of moisture in a subject's exhaled breath, particularly where the breath is exhaled through the mouth. As such, the device may further comprise a desiccant or humectant for removing or adding moisture to the exhaled breath prior to contact with the thermochemical reactant.

The measure of the biomarker in the breath as indicated to a user may be in the form of a concentration of the biomarker in the breath. The concentration may be determined from the measured rate of change in temperature in a number of ways. For example, the concentration of the biomarker in the breath may be based on a look up table of values correlating rates of change in temperature with concentrations of the biomarker. In another example, the concentration of the biomarker in the breath may be based on a mathematical model correlating rates of change in temperature with concentrations of biomarker.

The device may further comprise processing means for receiving data describing the measured rate of change in temperature and determining from the data the measure of the biomarker in the breath. The processing means preferably receives the data wirelessly. The processing means may further communicate a determined measure of the biomarker in the breath to the user interface.

In certain embodiments, the thermal sensor may comprise a temperature dependant colour change material, and wherein the indicated measure of the biomarker in the breath is based on the colour of the material at a predetermined period of time after the exhaled breath is introduced to the device.

The device may be configured to receive the exhaled breath from a subject's mouth. Additionally or alternatively, the device may be configured to receive the exhaled breath from a subject's nose.

The device may further comprising a reference thermal sensor positioned to measure background temperatures in the device. In this way, the rate of change in temperature measured by the thermal sensor can be adjusted to reflect any changes in temperature independent of the thermochemical reaction, for example changes in temperature caused by the exhaled breath.

There is further provided a method of monitoring a biomarker in an exhaled breath comprising:

contacting the exhaled breath with a sensing element comprising a thermochemical reactant that undergoes a thermochemical reaction with the biomarker;

measuring with a thermal sensor the rate of change in temperature caused by the thermochemical reaction; and determining from a measured rate of change in temperature a measure of the biomarker in the breath.

Optional features of the device described above are also optional to this method where appropriate.

BRIEF DESCRIPTION OF DRAWINGS

Embodiments of the present invention will now be described, by way of example only, with reference to the accompanying drawings, in which.

DESCRIPTION OF EMBODIMENTS

Figure 1:
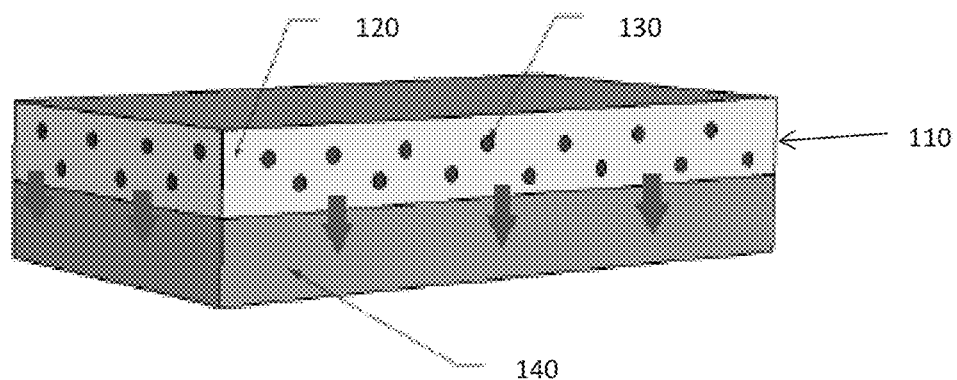
FIG. 1 is a perspective view of an arrangement of a sensing element and thermal sensor.

Referring to the drawings, there is provided a device 100 for monitoring biomarkers in exhaled breath. Biomarkers refer to specific compounds in the breath whose presence and quantity are indicative of certain diseases and/or physiological processes occurring in the body.

Figure 2:
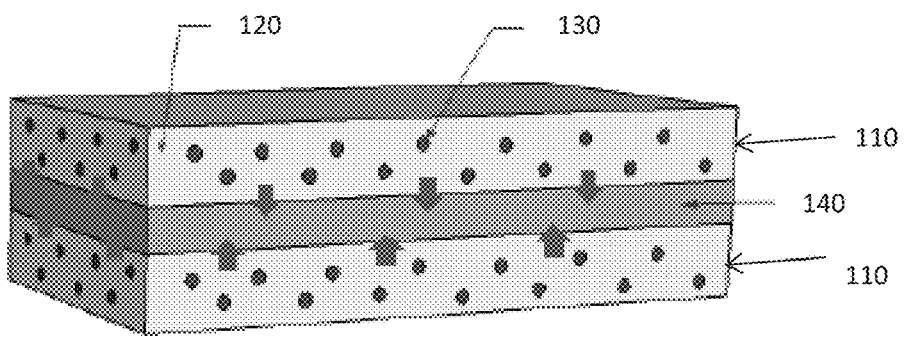
FIG. 2 is a perspective view of an alternate arrangement of a sensing element and thermal sensor.

Referring initially to FIGS. 1 and 2, a sensing element 110 is provided comprising a thermochemical reactant 120 for undergoing a thermochemical reaction with the biomarker of interest. That is, the thermochemical reactant 120 will be specific to the biomarker of interest, and selected such that the biomarker reacts with the thermochemical reactant 120 exothermically (releasing heat) or endothermically (absorbing heat). The rate at which heat is released or absorbed, i.e. the rate of change in temperature after the thermochemical reactant 120 has been exposed to exhaled breath, can be used to determine a measure of the biomarker in the breath.

As the concentrations of biomarkers in the breath can be small, the sensing element 110 may also comprise a sensitivity booster 130. The sensitivity booster 130 acts to accelerate and amplify the measured rate of change in temperature to increase the sensitivity of the device 100 and provide more accurate measures of the biomarker, particularly at low concentrations. The sensitivity booster 130 is a material that is selected to undergo a thermochemical reaction with a product of the reaction between the thermochemical reactant 120 and the biomarker.

To provide support to the thermochemical reactant 120, the sensing element 110 may also include a support element onto to which the thermochemical reactant 120 can be coated or impregnated. The support element may be substantially planar in shape, as seen for example in FIGS. 4c, 5, 6 and 10. Alternatively, the support element may be tubular as shown, for example, in FIGS. 7 to 9.

It will be appreciated that the selection of thermochemical reactant 120 will be dependent on the biomarker to be analysed as reactants that undergo thermochemical reactions with one biomarker may not undergo a reaction with another biomarker. Furthermore, it is desirable that the thermochemical reactant 120 selectively undergoes the thermochemical reaction with the biomarker of interest, and does not react with other compounds that may be found in exhaled breath. Following on from this, the selection of the sensitivity booster 130 will be dependent on the selected thermochemical reactant 120 and the products of reaction of the thermochemical reactant 120 with the biomarker of interest. For different biomarkers and different thermochemical reactants 120, the products of reaction will also differ and the sensitivity booster 130 will be selected as a material that undergoes a thermochemical reaction with the products of the initial reaction.

Figure 5:
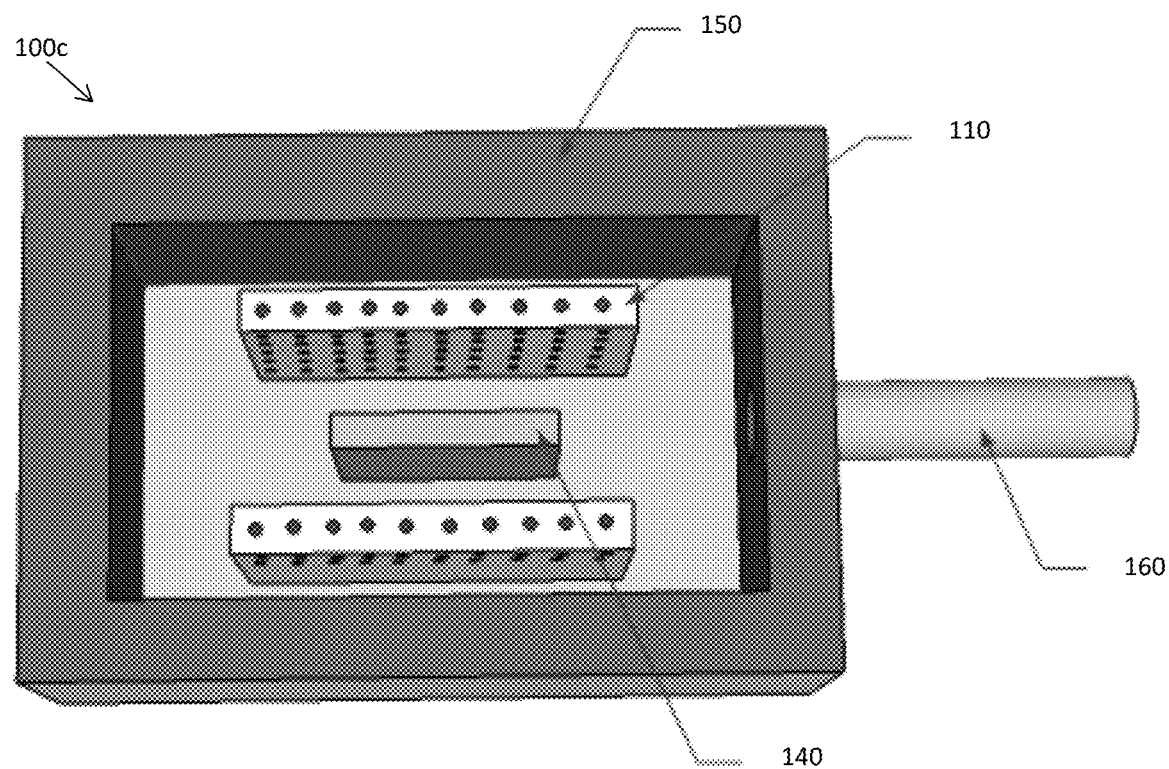
FIG. 5 is a perspective view of a third embodiment of a monitoring device.
Figure 6:
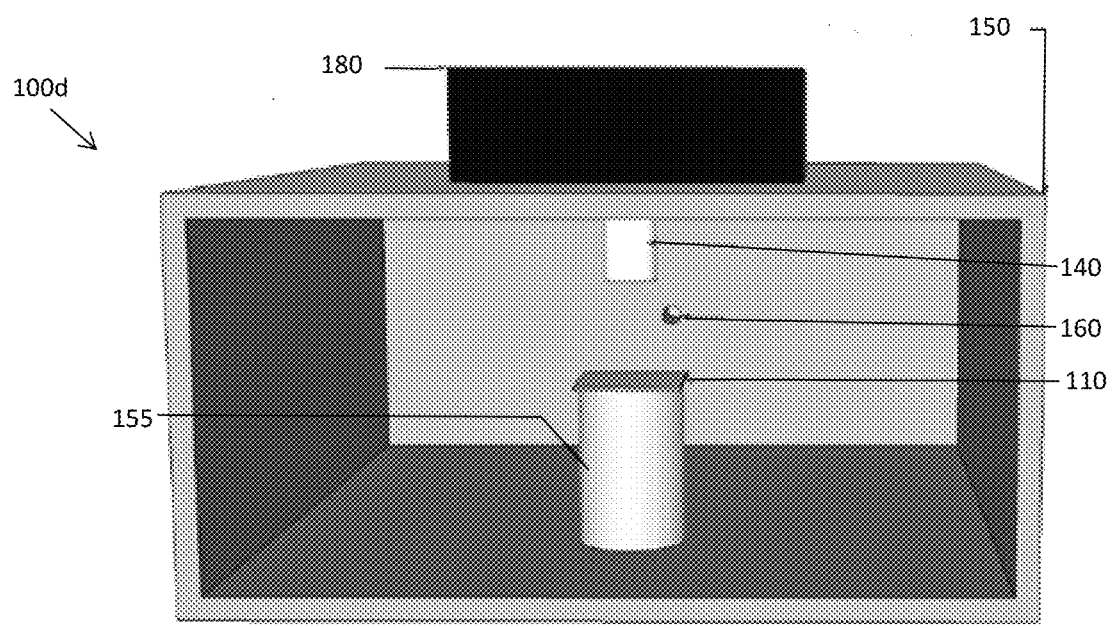
FIG. 6 is a perspective view of a fourth embodiment of a monitoring device.
Figure 7:
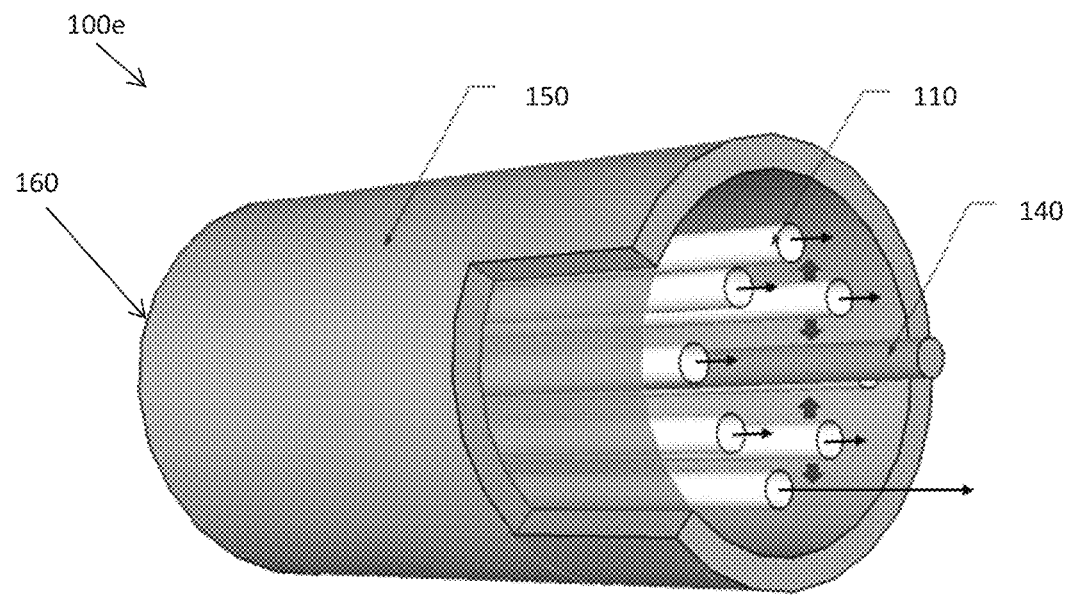
FIG. 7 is a perspective view of a fifth embodiment of a monitoring device.

A thermal sensor 140 is provided to measure the rate of change in temperature caused by the thermochemical reaction between the biomarker and the thermochemical reactant 120 and, where present, between the sensitivity booster 130 and a product of the initial thermochemical reaction. It will be appreciated that the thermal sensor 140 may be any suitable means for monitoring rates of change in temperature. For example, the thermal sensor 140 may be a contact temperature sensor type that is placed in contact with the thermochemical reactant 120 to monitor changes in temperature, such as is shown in FIGS. 1 and 2, or a non-contact temperature sensor type that monitors changes in temperature at a distance from the thermochemical reactant 120, for example as shown in FIGS. 5 to 7.

As shown in FIG. 1, the thermal sensor 140 may be in contact with the thermochemical reactant 120 at one surface. Alternatively, and to increase sensitivity of the device 100 by increasing the contact surface area between the thermochemical reactant 130 and the thermal sensor 140 without needing to increase the size of the thermal sensor 140, the thermal sensor 140 may be in contact with the thermochemical reactant 120 at two surfaces, as shown in FIG. 2.

As the sensitivity booster 130 is selected to react with a product of the thermochemical reactant 120 and the biomarker, the sensitivity booster 130 is configured to be in contact with the thermochemical reactant 120. For example, the sensitivity booster 130 may be dispersed throughout the thermochemical reactant 120, as shown in FIGS. 1 and 2.

The method of providing a thermochemical reactant 120 with the sensitivity booster 130 dispersed therethrough will depend on the physical properties of the selected thermochemical reactant 120 and sensitivity booster 130 for a specific system. Typically, a mixture of the thermochemical reactant 120 and the sensitivity booster 130 will be prepared which can be applied to a support element or directly to the thermal sensor 140. In some embodiments, an aqueous mixture containing the thermochemical reactant 120 and sensitivity booster 130 may be prepared and absorbed onto a porous support element. In other embodiments, a viscous mixture containing the thermochemical reactant 120 and sensitivity booster 130 may be prepared and coated onto a support element or directly onto the thermal sensor 140. In further embodiments, a particulate mixture containing the thermochemical reactant 120 and sensitivity booster 130 may be prepared and adhered to a support element or the thermal sensor 140.

Additionally or alternatively, the sensitivity booster 130 may be provided as at least one layer on the thermochemical reactant 120. As for the mixtures above, the method of providing a thermochemical reactant 120 with a layer of sensitivity booster 130 will depend on the physical properties of the selected thermochemical reactant 120 and sensitivity booster 130 for a specific system. Typically, the thermochemical material will be provided on a support element or directly on the thermal sensor 140. The sensitivity booster 130, which may be a liquid, particulate material or thin solid film, will then be applied to the thermochemical reactant 120. Multiple layers of the thermochemical reactant 120 and/or the sensitivity booster 130 may be provided which may accelerate and amplify the measured rate of change in temperature to increase the sensitivity of the device 100 and provide more accurate measures of the biomarker, particularly at low concentrations.

The sensing element 110 may be mounted in a housing 150 of the device 100, the housing having an inlet 160 for receiving a subject's exhaled breath. The inlet may comprise a one-way valve 165 to prevent the exhaled breath received into the device 100 from flowing back out through the inlet. The thermal sensor 140 may also be mounted in the housing 150 however it will be appreciated that in some embodiments the thermal sensor 140 may be located outside of the housing 150. It will be appreciated that the housing 150 is resealable and the inlet 160 may be configured to receive exhaled breath orally or nasally by the subject. Preferably, the sensing element 110 is removably mounted in the housing 150 such that the sensing element 110 can be replaced after each use without the need to replace the other components of the device 100.

Measures of the biomarker, such as the concentration, in an exhaled breath sample is determinable from the rate of change in temperature as measured by the thermal sensor 140. For example, a concentration of biomarker in the breath may be determined based on a look up table of values correlating rates of change in temperature with concentrations of the biomarker. Alternatively, a concentration of the biomarker in the breath may be determined based on a mathematical model correlating rates of change in temperature with concentrations of biomarker. These correlations between rates of change in temperature and concentration may be determined by completing a series of calibration measurements of gases of various known concentrations of the biomarker of interest.

In some instances, in order to determine the concentration of the biomarker in the breath, the volume of the exhaled breath received by the device 100 may also be required. To determine the volume of exhaled breath, the device 100 may be configured to receive a known volume of gas. For example, in the embodiments of the device 100a and 100b of FIGS. 4a and 4b, the sensing element is provided in a collapsible plastic bag into which the subject exhales breath via the inlet 160, inflating the bag to a maximum size of known volume. To reduce variations of the volume of exhaled breath received by the device, a check valve 165 is provided to prevent back flow of the exhaled breath from the device. In other embodiments, a flow meter (not shown) positioned near the inlet 160 may be used to measure the rate of flow of exhaled breath into the device 100 and the volume of breath entering the device determined from the flow rate and cross-sectional area of the inlet 160. In further embodiments, the exhaled breath may be collected in a collapsible container of known volume after which the collapsible container is placed in fluid communication with the device 100 such that the collected breath flows from the collapsible container into the device 100.

Another factor that may affect the rate of change in temperature could be the moisture content in the exhaled breath, which can vary significantly from subject and the source of exhaled breath, i.e. orally or nasally. To address the variations in moisture content, desiccant or humectant may be provided at the inlet 160 for removing or adding moisture to the exhaled breath. The preferred moisture content in the exhaled breath may vary, depending on a number of factors such as the sensitivity of the thermochemical reactant 120 and the sensitivity booster 130 to water. That is, in some embodiments the thermochemical reactant and/or sensitivity booster may react or degrade when in contact with water, such that a desiccant is provided to remove moisture from the exhaled breath prior to its contact with the sensing element 110. In other embodiments, a humectant may be used for thermochemical reactants 120 and/or sensitivity boosters where the presence of certain levels of moisture in the breath may improve sensing of the biomarker.

The rate of change in temperature may also be affected by other temperature changes occurring in the device, for example temperature changes occurring due to the temperature of the user's exhaled breath or evaporation of moisture found in the exhaled breath. To measure changes in background temperatures, the device 100 may further comprise a reference thermal sensor 145 positioned to measure background temperatures in the device. The reference thermal sensor 145 may positioned spaced apart from the sensing element 110. The rate of change in temperature measured by the thermal sensor can then be adjusted to reflect changes in temperature independent of the thermochemical reaction occurring at the sensing element.

Figure 4A:
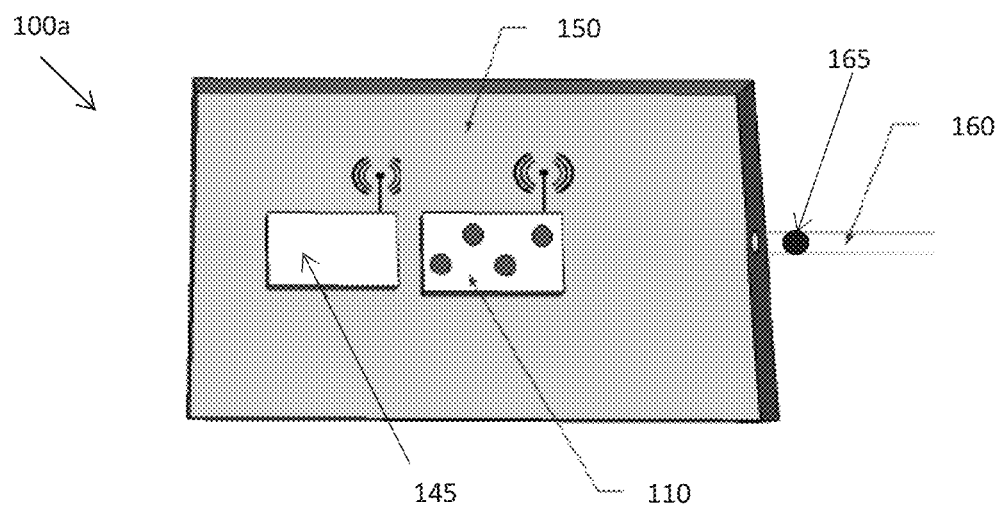
FIGS. 4a and 4b are top views of second embodiments of a monitoring device.
Figure 4B:
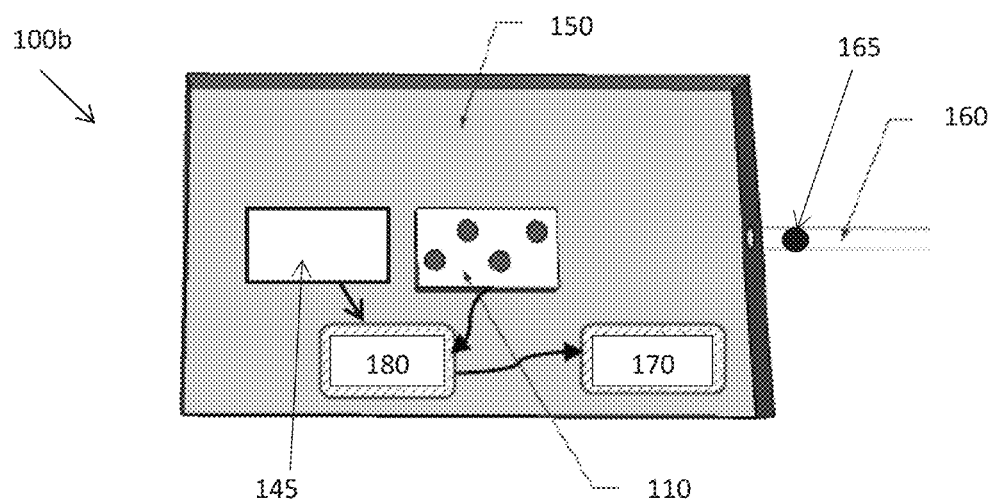

The device 100 further includes a user interface 170 for indicating to a user the measured concentration of the biomarker in the exhaled breath as determined from the measured rate of change in temperature. Processing means 180 may be provided for receiving data describing the measured rate of change in temperature and determining from that data the concentration of the biomarker. The processing means 180 may receive the data wirelessly, as shown in FIG. 4a, or be directly connected with the thermal sensor for receiving the temperature data, as shown in FIG. 4b.

Once the processing means 180 has received the data and determined from the data a measure of the biomarker, the processing means 180 communicates the determined measure of the biomarker to the user interface 170 such that the measured concentration can be indicated to the user. The determined measure may be communicated from the processing means 180 to the user interface directly, as shown in the device 100b of FIG. 4b, wirelessly, or via one or more connectors 190 on the processing means 180, for example as shown in the devices 100g and 100h of FIGS. 9 and 10, for direct physical connection with a user interface 170. In a preferred embodiment, the processing means 180 and/or the user interface 170 are external to the housing 150, such as a mobile phone for receiving and displaying the determined measure to the user.

In an alternate embodiment, the thermal sensor is a temperature dependant colour change material. For example, one or more leuco dyes such as spirolactones, fluorans, spiropyrans and fulgides may be coated on the thermochemical reactant or dispersed in the thermochemical reactant. As the thermochemical reactions proceed, the material changes in colour to reflect the temperature of the sensing element. In this way, a user can determine the rate of change in temperature based on the colour of the material a predetermined period of time after the exhaled breath is introduced to the device, for example by comparison of the material with a colour chart. Alternatively, a camera could be used to detect any colour changes as they occur. The temperature dependent colour change material may be configured to display a progression through a plurality of colours as the temperature rises. Alternatively, the temperature dependent colour change material may be configured to only change colour once a predetermined threshold temperature had been exceeded.

Various embodiments of the device 100 will now be discussed with reference to FIGS. 3 to 12.

Figure 3:
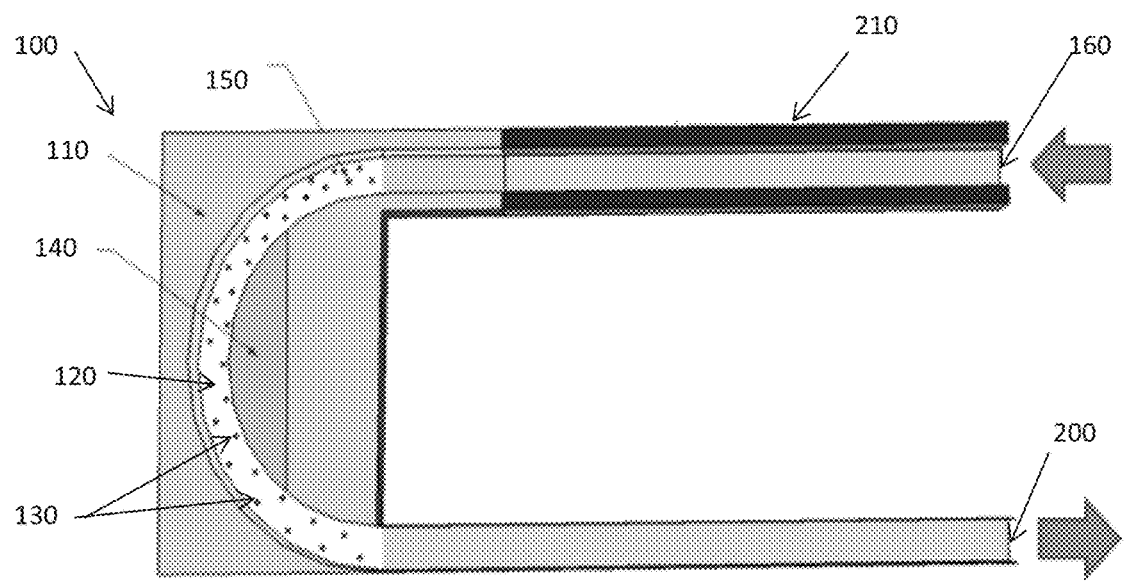
FIG. 3 is a top view of a first embodiment of a monitoring device.

Referring to FIG. 3, there is provided a first embodiment of a device 100 for monitoring a biomarker in exhaled breath. The device comprises an inlet 160 for receiving a subject's exhaled breath. The inlet 160 is provided with a temperature control layer 210 for heating or cooling the exhaled breath to a desired initial temperature prior to entering a U-shaped tubular sensing element 110 coated with the thermochemical reactant 120 and sensitivity booster 130 on its inner surface. Pre-heating or cooling the exhaled breath to a desired initial temperature can assist in providing more accurate measurements of the biomarker as a result of a known initial temperature and removes variations in exhaled breath temperature received from different subjects to be monitored.

As the exhaled breath flows through the sensing element 110, rate of change of temperature caused by the thermochemical reaction between the biomarker and the thermochemical reactant 120, and the subsequent thermochemical reaction between the sensitivity booster 130 and a product of the initial reaction, is measured by a thermal sensor 140 located on the inner curvature of the sensing element 110. The sensing element 110 and the thermal sensor are mounted in a thermally insulated housing 150 for insulation against ambient air variations. The measured rate of change in temperature can then be used to determine a measure of the biomarker in the exhaled breath.

Figure 4C:
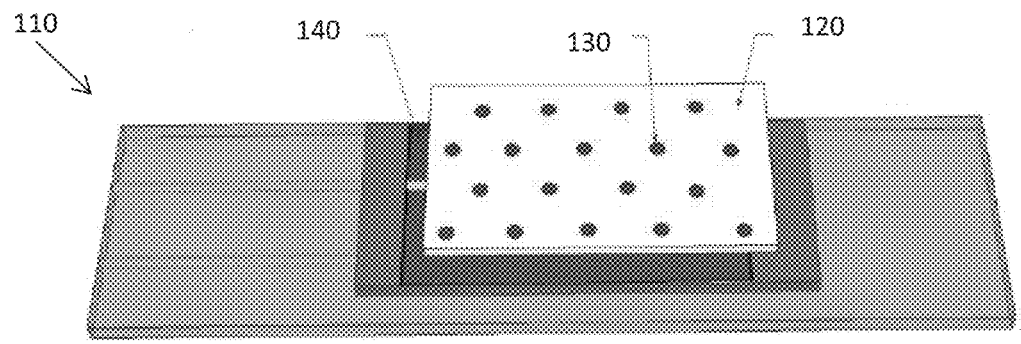
FIG. 4c is an exploded perspective view of a sensing element for the monitoring devices of FIGS. 4a and 4b.

Referring to FIGS. 4a to 4c, there is provided second embodiments of a device 100a and 100b for monitoring a biomarker in exhaled breath. A planar sensing element 110 is provided comprising a thermal sensor 140 coated in a mixture of the thermochemical reactant 120 and sensitivity booster 130. In some embodiments, a thin layer of a thermally conductive material may be positioned between the thermal sensor 140 and the thermochemical reactant 120 in order to protect the thermal sensor 140.

The devices 100a and 100b comprise a housing 150 in the form of a collapsible plastic bag of known volume. A sensing element 110 including the thermal sensor and reference thermal sensor are mounted centrally inside the housing 150. A subject exhales into the inlet 160 such that the bag inflates to its maximum size and the thermal sensor measures the resulting rate of change in temperature at the sensing element 110. Simultaneously, the reference thermal sensor 145 measures the background temperature in the device. In the device 100a of FIG. 4a, data describing the measured rate of change in temperature and measured background temperature is wirelessly transmitted to a processing device. In the device 100b of FIG. 4b, the data is directly transmitted to the processing device 180 and the resulting measure of the biomarker in the breath as determined by the processor is directly communicated with a user interface 170 for indicating to a user the determined measure.

Referring to FIG. 5, there is provided a third embodiment of a device 100c for monitoring a biomarker in exhaled breath. The device 100c comprises a sealed housing 150 of known volume formed of a thermal insulating material. A pair of sensing elements are positioned in spaced arrangement on two sides of a non-contact temperature sensor 140. The exhaled breath enters the device 100c via inlet 160.

Referring to FIG. 6, there is provided a fourth embodiment of a device 100d for monitoring a biomarker in exhaled breath. The device 100d comprises a sealed housing 150 of known volume formed of a thermal insulating material. The device 100d further comprises a stand 155 onto which a sensing element 110 is placed. A thermal sensor 140 in the form of an infrared (IR) sensing head is positioned in a spaced arrangement from the sensing element 110. The exhaled breath enters the device 100d via inlet 160 and the temperature of the sensing element is monitored by the IR sensor head 140.

Referring to FIG. 7, there is provided a fifth embodiment of a device 100e for monitoring a biomarker in exhaled breath. In the device of FIG. 6, a tubular housing 150 is provided with a plurality of tubular sensing elements 110 mounted to increase the exposure of the thermal sensor 140 to the tubular sensing elements 110, such as concentrically about a centrally positioned thermal sensor 140.

Figure 8:
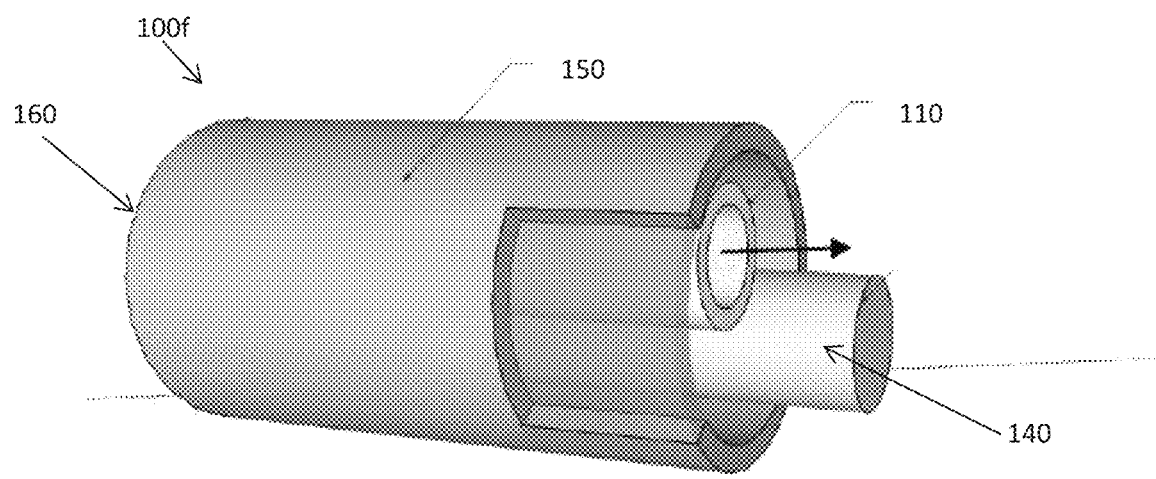
FIG. 8 is a perspective view of a sixth embodiment of a monitoring device.

Referring to FIG. 8, there is provided a sixth embodiment of a device 100f for monitoring a biomarker in exhaled breath. The device 100f comprises a tubular housing 150 in which a single tubular sensing element 110 and a thermal sensor 140 are mounted non-concentrically.

Figure 9:
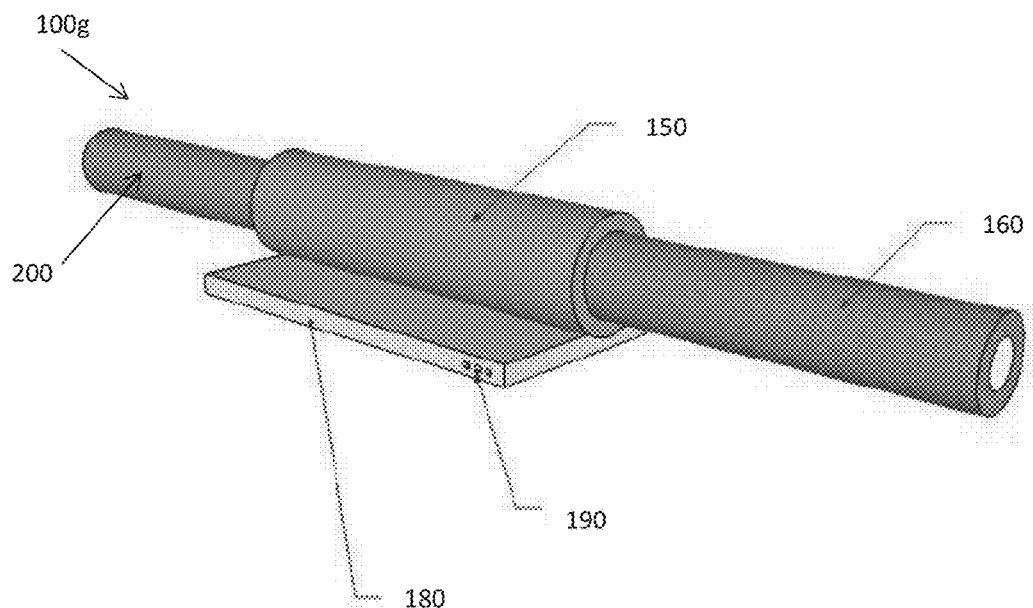
FIG. 9 is a perspective view of a seventh embodiment of a monitoring device.

Referring to FIG. 9, there is provided a seventh embodiment of a device 100g for monitoring a biomarker in exhaled breath. The device 100g is provided with an inlet 160 and an outlet 200 in fluid communication with a tubular housing 150 in which the sensing element 110 and thermal sensor 140 are mounted. The sensing element 110 and thermal sensor 140 may be mounted in any suitable configuration, such as the configurations shown in FIGS. 7 and 8. In another example, a tubular thermal sensor 140 may be mounted on the inner surface of the housing 150 and a tubular sensing element 110 mounted on the inner surface of the thermal sensor therefore forming concentric tubes.

A processing means 180 in the form of an integrated circuit is mounted on the housing for receiving data describing the measured rate of change in temperature from the thermal sensor 140 and determining from that data a measure of the biomarker. The processing means 180 comprises a plurality of connectors 190 for docking with a user interface 170 such as a mobile device or computer and communicating the determined measure of the biomarker such that the determined measure can be indicated to the user. It will be appreciated that connectors 190 could alternatively be replaced with means for wirelessly communicating with the user interface 170.

The device 100g may further comprise a flow meter used to measure the rate of flow of exhaled breath into the device. Alternatively, the device 100g may further comprise a collapsible container of known volume in fluid communication with the outlet 200 for ensuring a known volume of exhaled breath flows through the sensing element 110.

Figure 10:
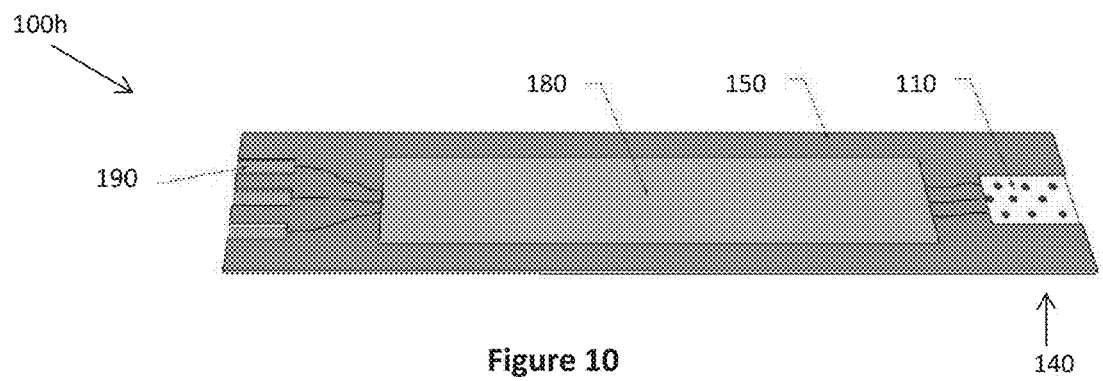
FIG. 10 is a perspective view of an eighth embodiment of a monitoring device.

Referring to FIG. 10, there is provided an eighth embodiment of a device 100h for monitoring a biomarker exhaled in the breath. The device 100h is configured as a planar rectangular strip comprising a planar sensing element 110 at one end mounted on a similarly sized and shaped thermal sensor 140. The thermal sensor is in communication with a processing means 180 for receiving data describing the measured rate of change in temperature from the thermal sensor 140. The device further comprises a plurality of connectors 190 in communication with the processing means 180 to communicate with a user interface 170 in a manner as described for device 100g above.

The device of 100h is designed to be lightweight and portable. Preferably, the device 100h is made from low cost materials such that the entire device 100h is disposable. Alternatively, the sensing element 110 is removably mounted to the housing 180 such that the sensing element 110 removed and replaced after use and the device 100h can then be re-used. The device 100h is configured to be removably mounted in any suitable housing for receiving a subject's breath such as a plastic bag of the type shown in FIGS. 4a and 4b, or in a housing as shown in FIG. 11.

Figure 11:
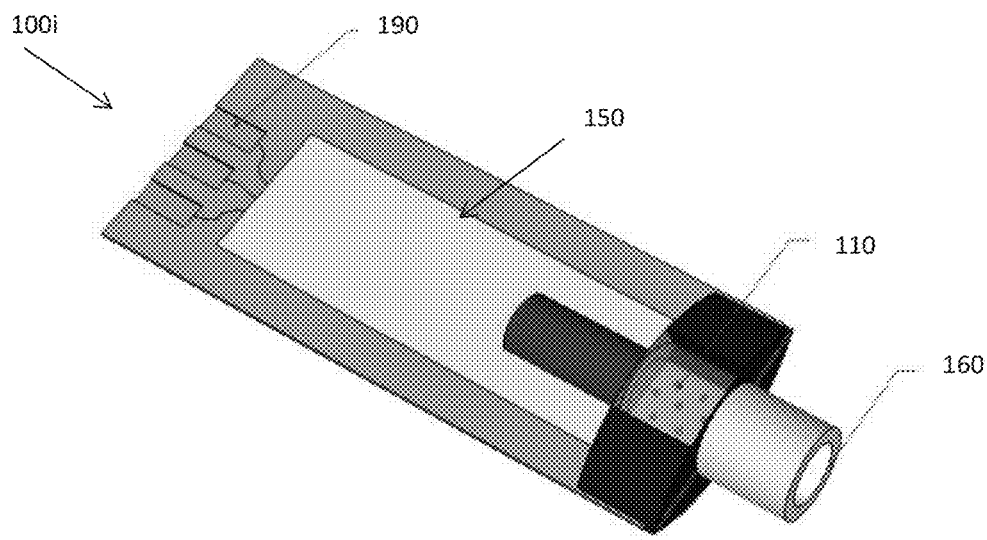
FIG. 11 is a perspective view of a ninth embodiment of a monitoring device.

Referring to FIG. 11, there is provided a ninth embodiment of a device 100i for monitoring a biomarker exhaled in the breath. The device 100i of FIG. 11 is similar to the device 100h of FIG. 10, however the housing 150 is configured to capture a known volume of the subject's breath. An inlet 160 is provided for receiving the breath and may be sized and shaped to fit in a subject's nostril to receive the exhaled breath nasally. The housing may be formed of a plastics material by any suitable method such as extrusion or blow moulding to achieve the desired shape. The inlet 160 may be removably attached to the housing 160 to allow access to the sensing element 110 for removal and replacement after each use.

Figure 12:
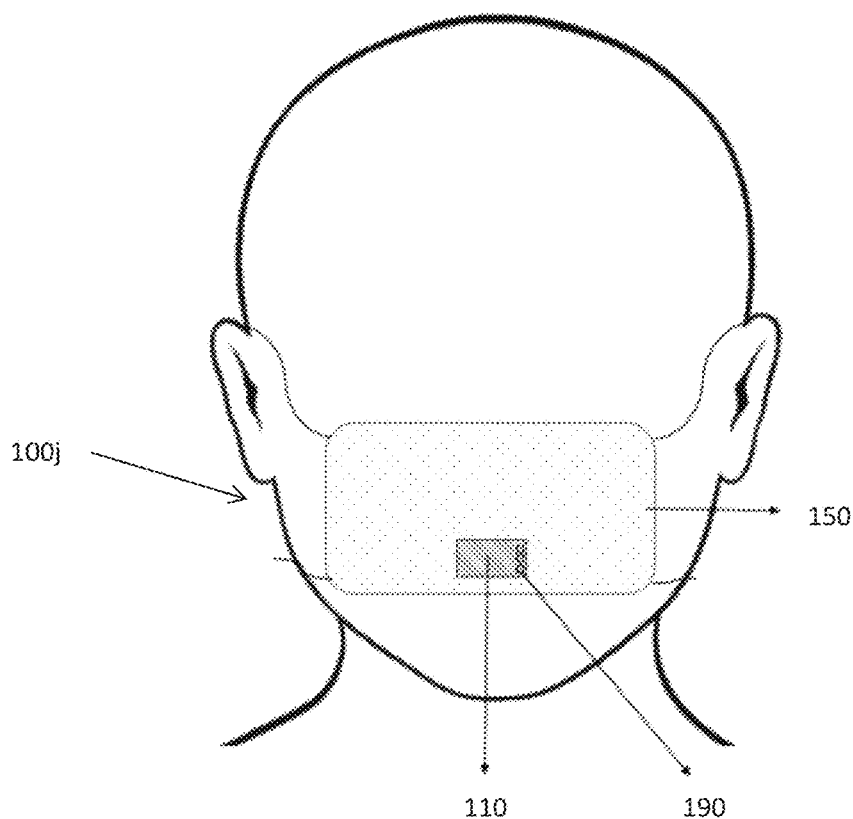
FIG. 12 is a front view of a tenth embodiment of a monitoring device as worn by a subject.

Referring to FIG. 12, there is provided a tenth embodiment of a device 100j for monitoring a biomarker exhaled in the breath. The device 100j comprises a housing 150 in the form of a face mask to be worn over a subject's nose and/or mouth. The sensing element 110, thermal sensor 140, processing means 180 and connector pins 190 are positioned on the mask in a way such that exhaled breath passes over the sensing element. The device 100j may further comprise a flow meter used to measure the rate of flow of exhaled breath over the sensing element. The measure of the biomarker in the breath can then be determined and displayed to a user in a manner as described above.

Figure 13:
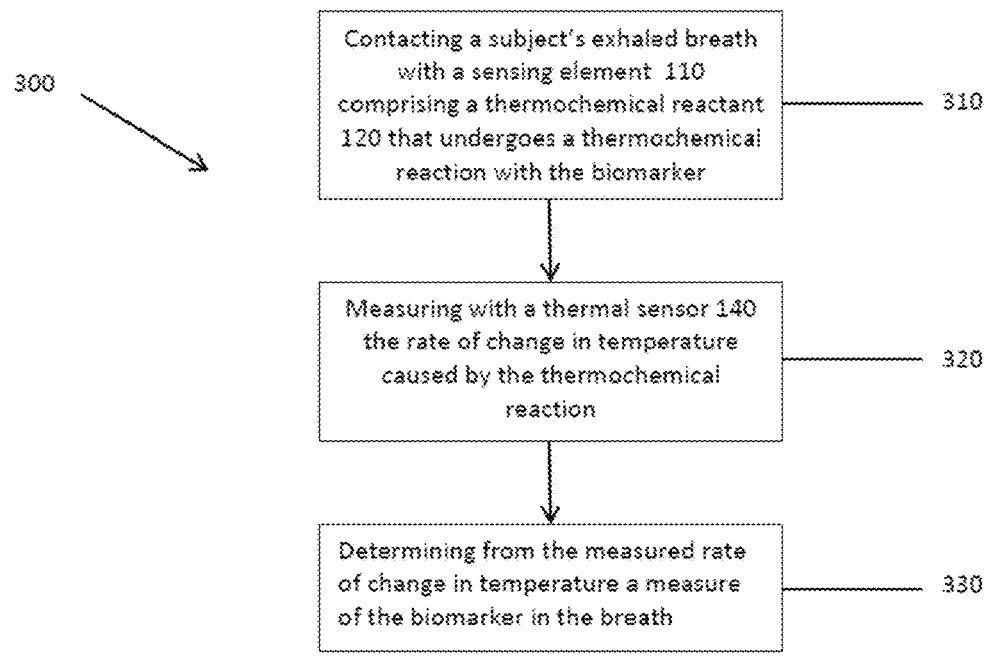
FIG. 13 is a flow diagram for a method of monitoring a biomarker in exhaled breath

Referring to FIG. 13, there is further provided a method 300 of monitoring a biomarker in exhaled breath comprising the steps of: contacting a subject's exhaled breath with a sensing element 110 comprising a thermochemical reactant 120 that undergoes a thermochemical reaction with the biomarker 310; measuring with a thermal sensor 140 the rate of change in temperature caused by the thermochemical reaction 320; and determining from the measured rate of change in temperature a measure of the biomarker in the breath 330.

EXAMPLES

Sensing Element for Monitoring Acetone

In one example, a device 100 is provided for monitoring levels of acetone (($CH_3$)$_2$CO) in the breath for the monitoring of ketone and insulin levels in type 1 diabetics. Hydroxylamine hydrochloride ($NH_3OH.HCl$) is selected as the thermochemical reactant 110, which undergoes the following exothermic reaction with acetone to produce hydrochloric acid (HCl) and heat.

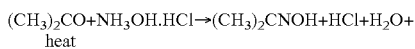

A second stage exothermic reaction then occurs between the hydrochloric acid produced above and the sensitivity booster 130 in the form of aluminium in accordance with the following reaction:

In addition to providing the second stage exothermic reaction, the metal aluminium particles also assist in heat transfer to the thermal sensor due to their high thermal conductivity and low specific heat capacity.

Fibre Bragg Grating (FBG) Sensor

A sensing element 110 for monitoring acetone was prepare using a 1 cm×1 cm piece of high quality ultrathin tissue as the support element. The tissue was dipped in a saturated solution of the thermochemical reactant 120, hydroxylamine hydrochloride (($NH_3OH.HCl$), before being contacted with the sensitivity booster 130, aluminium powder (Al), to create a layer of aluminium powder on the hydroxylamine hydrochloride. The sensing element 110 was then left to air dry.

A fibre optic sensor comprising a fibre Bragg grating (FBG) sensor was selected as the thermal sensor 140. The FBG sensor head was placed into the centre of a housing 150 comprising a 1 L volume plastic bag surrounded by polystyrene cystosepiment insulating material. The dried sensing element 110 was placed on top of the FBG sensor head to cover the FBG sensing area.

Gas samples containing a known concentration of acetone were prepared by dropping a known amount of acetone liquid, as measured by a high precision pipette, into a container of known volume.

Under laboratory conditions at a room temperatures of between 20 to 25° C., the pre-prepared gas samples were then introduced into the plastic bag. The reflected light from the FBG sensor as the thermochemical reactions progressed was passed through an optical edge filter and the optical power (dB) of the light exiting the edge filter was measured using an optical power meter. The optical power of the reflected light from the FBG sensor head, which corresponds to the temperature at the FBG sensor head was measured over a period of approximately 8 minutes after introduction of the gas sample to the plastic bag. The sampling was repeated three times each with gas samples comprising 2 ppm and 4 ppm of acetone. The results are shown in FIG. 13a.

Figure 14A:
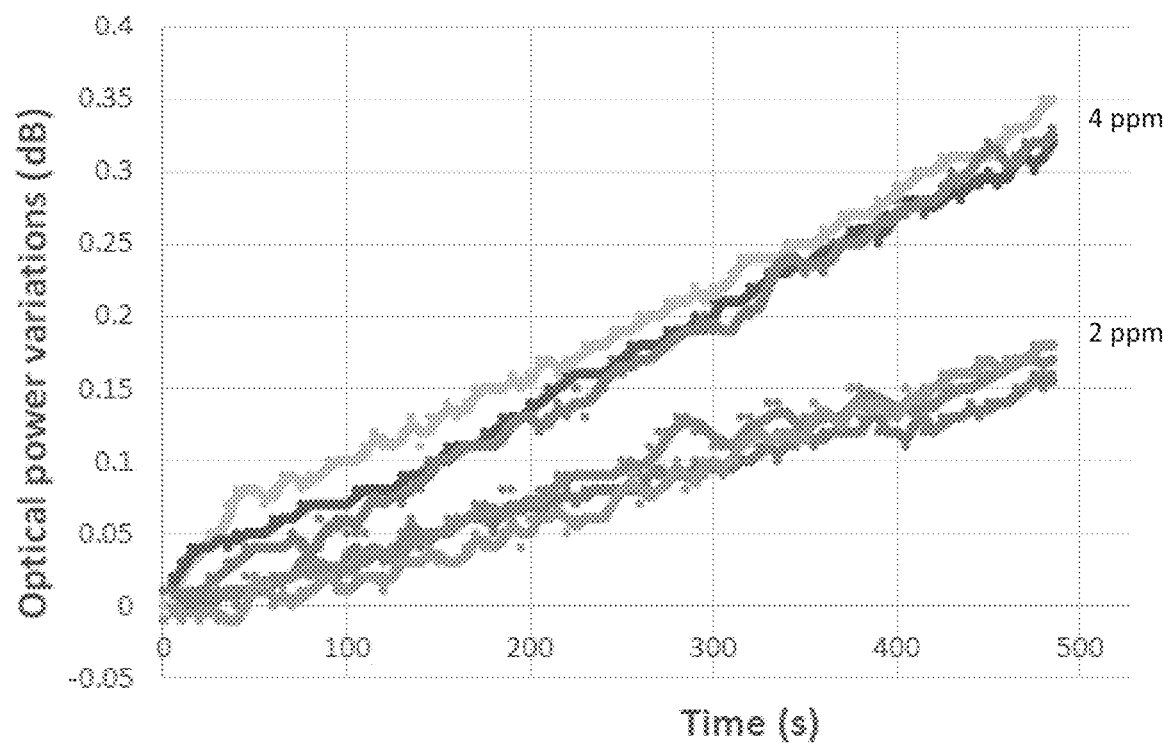
FIGS. 14a-14c are graphs depicting the rate of change in temperature monitored with an optical temperature sensor for an air bag monitoring device.
Figure 14B:
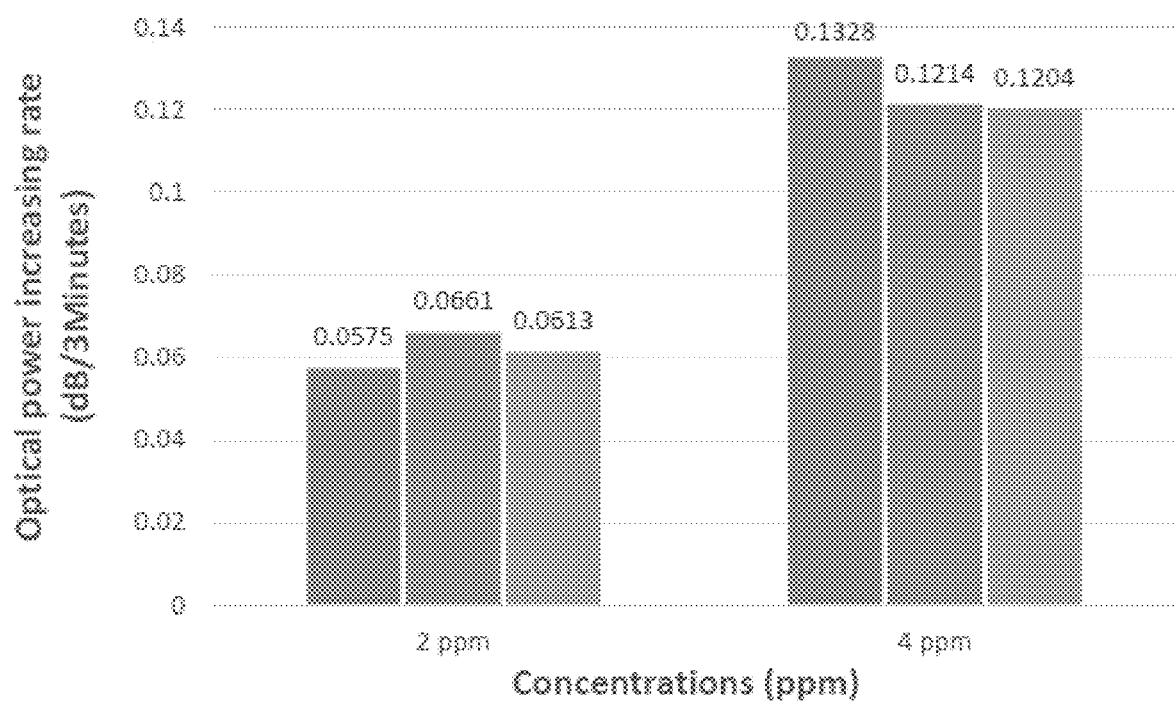

FIG. 14a shows that the increase in optical power variation (dB), and thus the increase in temperature, for the 2 ppm and 4 ppm gas samples were substantially linear over the monitoring period. FIG. 14b provides a summary of the results of FIG. 13a, showing the relationship rate of change in optical power, which correlates with the rate in change in temperature, calculated as the value measured at 3 minutes divided by 3 minutes.

Figure 14C:
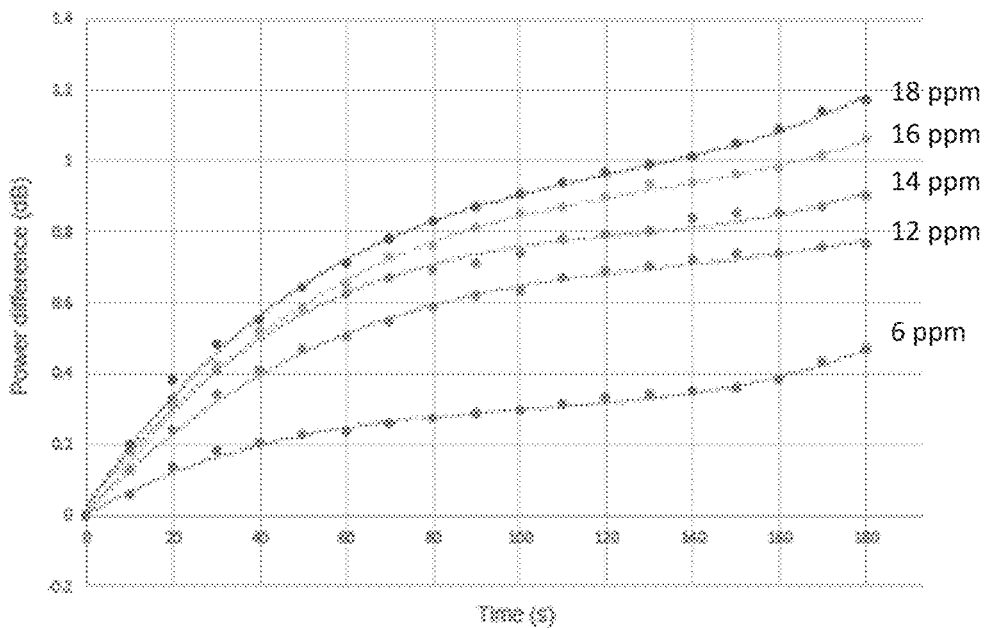

The above experiments were also conducted for higher acetone concentrations, i.e. 6, 12, 14, 16 and 18 ppm, the results of which are shown in FIG. 14c. As can be seen by FIG. 14c, as the concentration of acetone increases the rate of change in temperature also increases. However, unlike the results shown for lower concentrations in FIG. 14a, the change in temperature over a three minute period is no longer linear but rather displays an inverse exponential growth where the rate of change in temperature decreases as time increases.

Figure 15A:
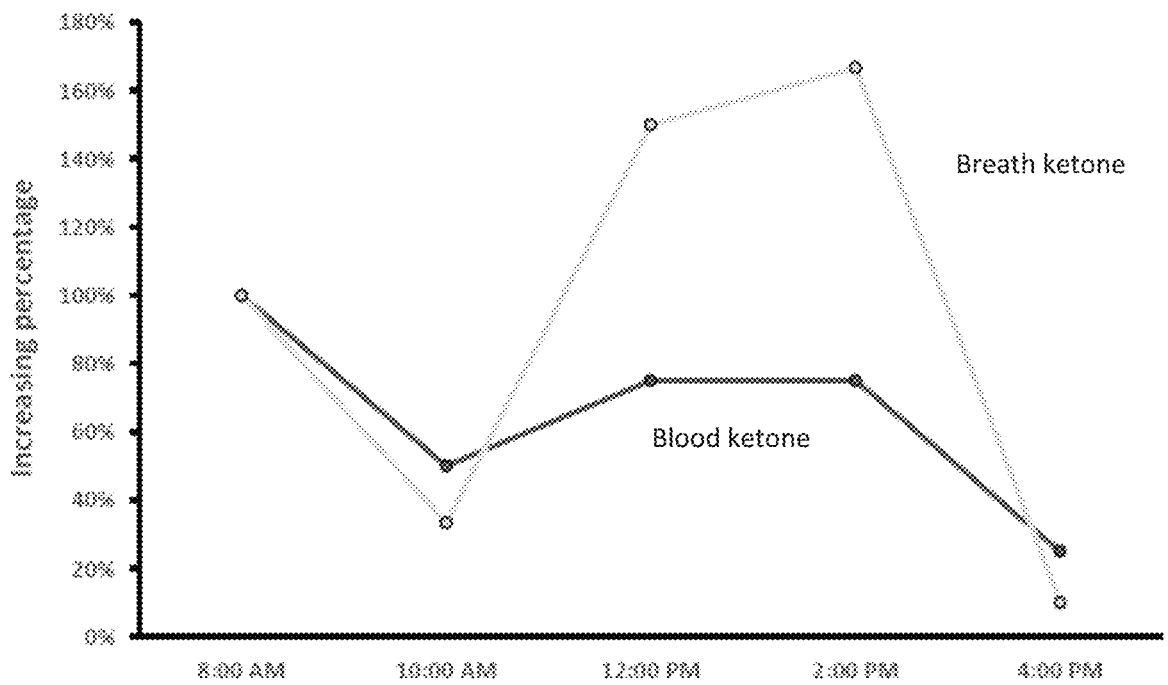
FIGS. 15a and 15b are graphs depicting the correlation between breath ketone measurements using an optical temperature sensor for an air bag monitoring device and measured blood ketone levels.
Figure 15B:
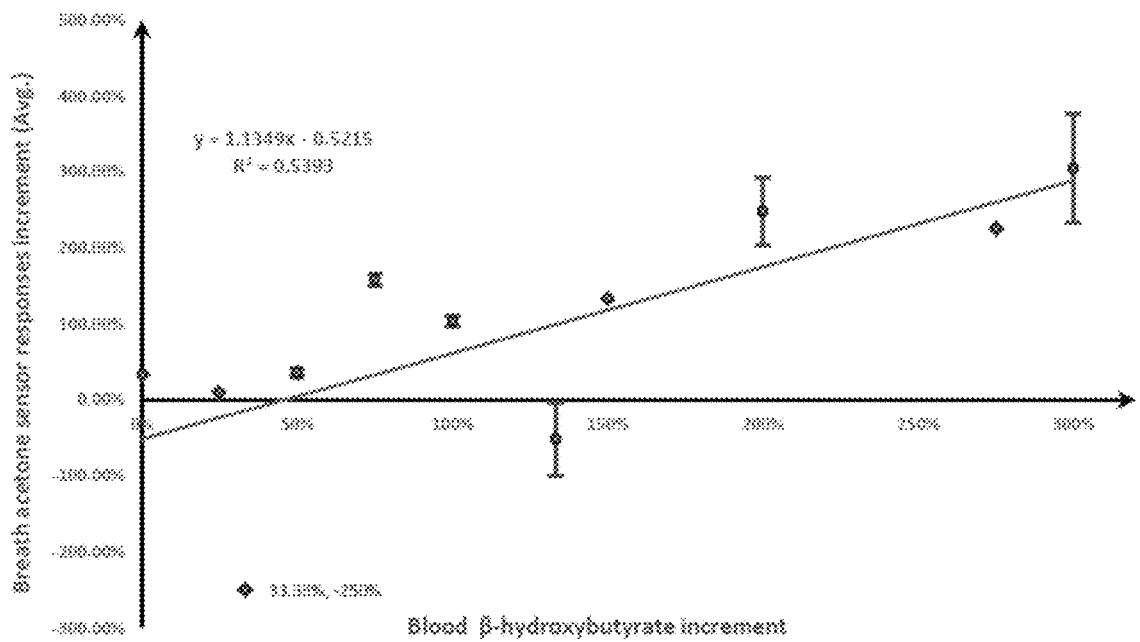

Further experiments were conducted using the FBG sensor on exhaled breath from human participants undergoing fasting. The participants fasted overnight, after which blood and breath samples were taken. Additional samples were taken throughout the day as the participants continued to fast, and again after the participants had broken the fast. As seen in FIG. 15a depicting the results for one participant, the determined change in ketone levels in the breath as measured by the FBG sensor followed the trend of the change in ketone levels in the blood. The results across the group of participants, as shown in FIG. 15b, further shows that the sensing response from the FBG sensor is directly proportional to the blood ketone levels.

Infrared (IR) Sensor

Figure 16A:
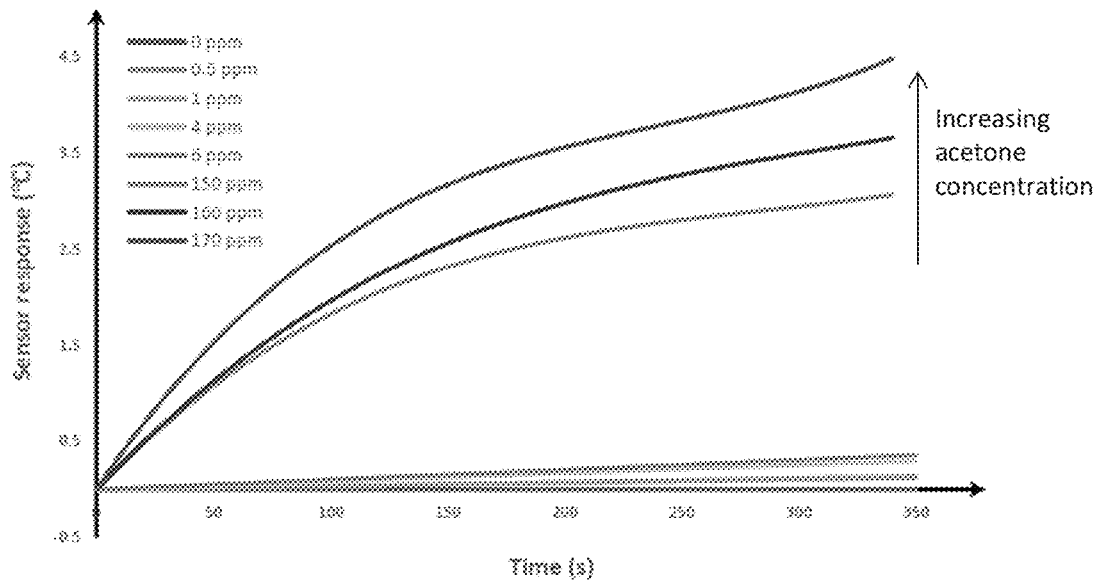
FIGS. 16a and 16b are graphs depicting the rate of change in temperature monitored with infrared (IR) temperature sensor.
Figure 16B:
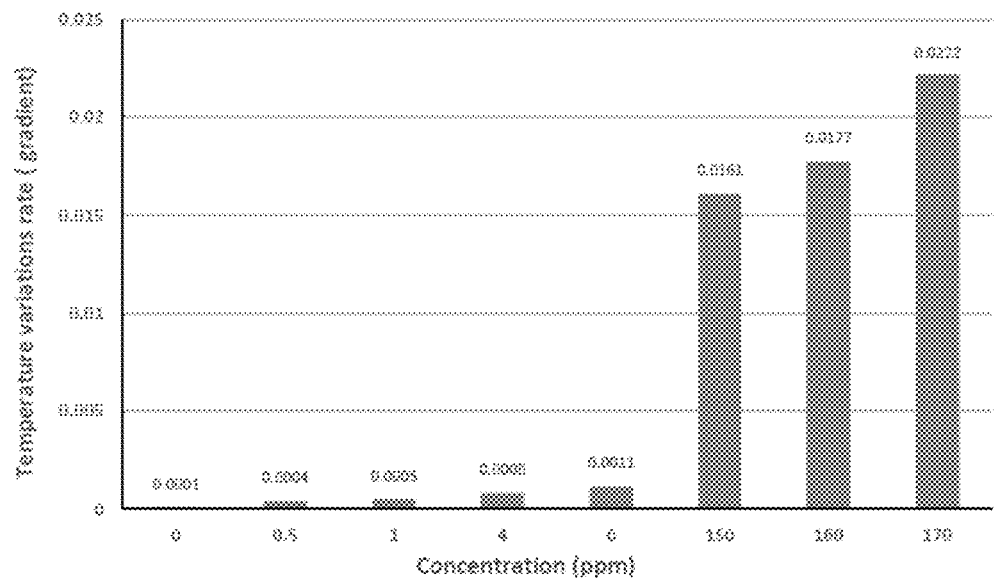

Additional experiments were conducted using an infrared (IR) sensor as shown in FIG. 6. A sensing surface of size 1.5 cm×1.5 cm was placed on the stand 155 in the centre of the housing 150, 1.5 cm below the IR sensor 140. Gas samples containing a known concentration of acetone from 0 to 170 ppm were prepared and introduced into the device and the temperature of the sensing element measured over time by the IR sensor head 140. As with the FBG sensor, as shown in FIG. 16a, the IR sensor was able to track the change in temperature after the introduction of the gas sample into the device to show that the rate of change of temperature increases with the concentration of acetone in the gas sample. The results rate of change over the initial 3 minutes of the results of FIG. 16a are summarised in FIG. 16b.

Digital Thermometer Sensor

Further experiments were conducted in devices using an ADT7420 digital thermometer in contact with a 1.5 cm×1.5 cm sensing surface comprising hydroxylamine hydrochloride (($NH_3OH.HCl$). An additional ADT7420 digital thermometer was provided in order to measure background temperature variations. The digital thermometers were placed into the centre of a housing 150 comprising a plastic bag surrounded insulating material.

Figure 17:
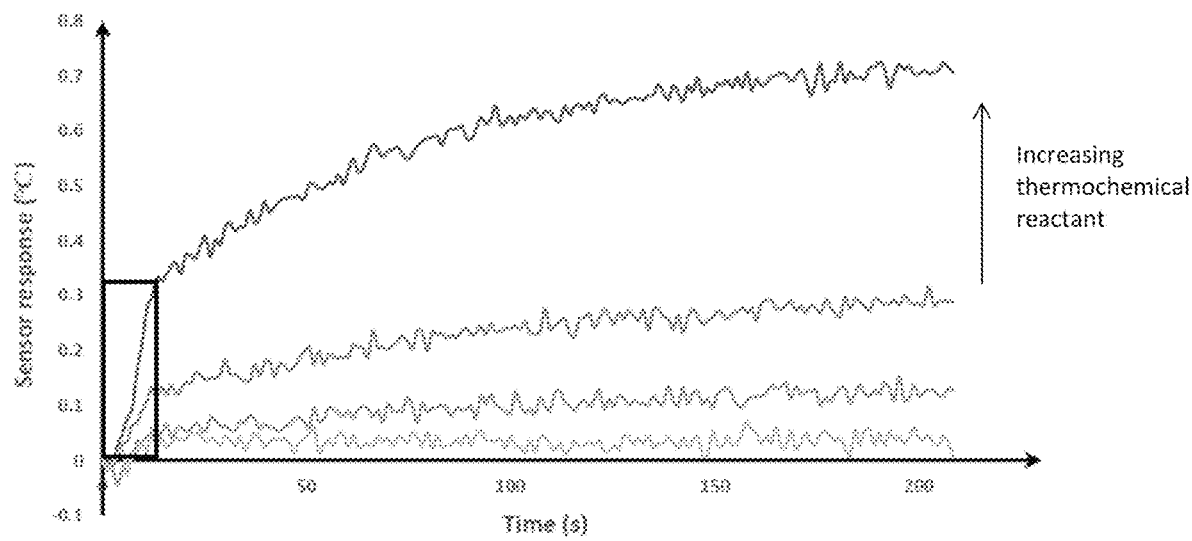
FIG. 17 is a graph depicting the rate of change of temperature for different quantities of thermochemical reactant.

The effect on the quantity of the thermochemical reactant hydroxylamine hydrochloride (($NH_3OH.HCl$) on the rate of change of temperature were investigated for gas samples having the same concentration of acetone (approximately 3 ppm). As can be seen from FIG. 17, as the quantity of the thermochemical reactant was increased from 3.5 mg to 28 mg, a more pronounced increase in temperature was observed.

Figure 18:
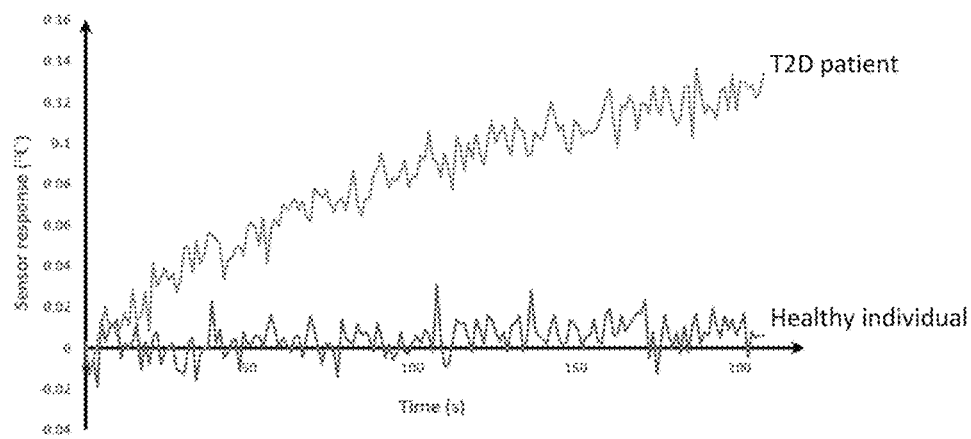
FIG. 18 is a graph depicting comparing the rate of change of temperature monitored with a digital temperature sensor between a health individual and an individual with type 2 diabetes (T2D)

FIG. 18 shows the measured response between breath samples obtained from a healthy individual who was not on a diet at the time of providing the breath sample, and a type 2 diabetes (T2D) patient on a ketogenic diet at the time of providing the breath sample. As can be seen from FIG. 18, the sensor recorded a noticeable change in temperature for the breath sample from T2D patient, indicating the presence of acetone in the breath as would be expected.

Figure 19A:
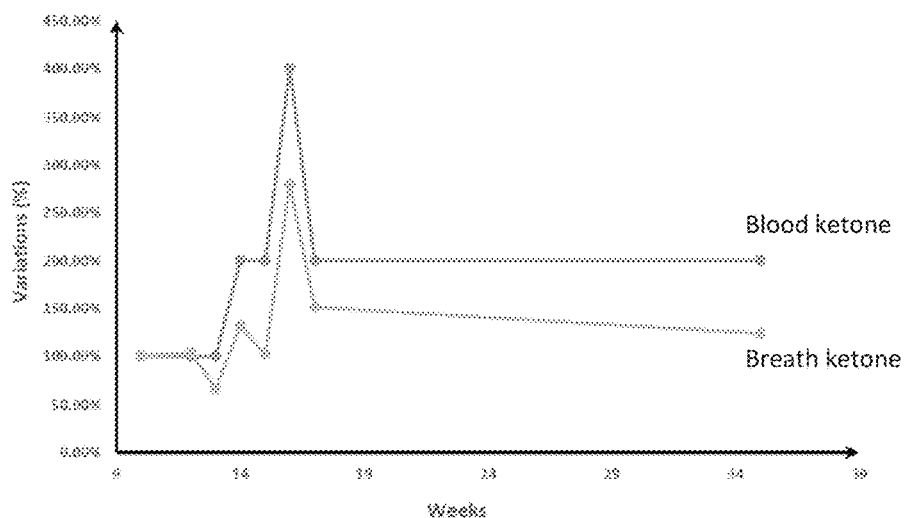
FIGS. 19a and 19b are graphs depicting the correlation between breath ketone measurements using a digital temperature sensor for an air bag monitoring device and measured blood ketone levels.
Figure 19B:
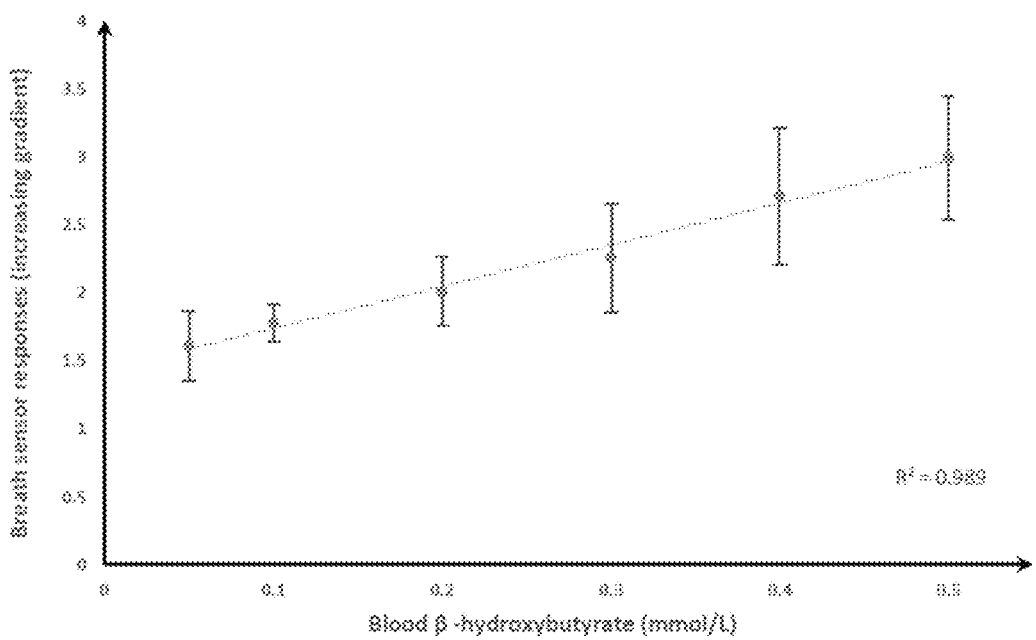

Further experiments were conducted using the digital thermometer sensor on exhaled breath from human participants undergoing a very low energy diet. VLEDs are low total energy and low carbohydrate diets that are associated with ketosis. Blood and breath samples were taken over the period of a number of weeks. FIG. 19a shows a comparison of the determined change in ketone levels in the breath as measured by the digital thermometer sensor and the change in ketone levels in the blood for one participant. The results across the group of participants, as shown in FIG. 19b, further shows that the sensing response from the digital thermometer sensor is directly proportional to the blood ketone levels.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A device for monitoring a biomarker in an exhaled breath, the device comprising:
    a sensing element comprising:
        a thermochemical reactant that undergoes a thermochemical reaction with the biomarker, and
        a sensitivity booster in contact with the thermochemical reactant, wherein the sensitivity booster undergoes a second thermochemical reaction with a product of the reaction between the thermochemical reactant and the biomarker;
    a thermal sensor positioned to measure a rate of change in temperature caused by the thermochemical reaction; and
    a user interface for indicating to a user an indicated measure of the biomarker in the exhaled breath, wherein the indicated measure of the biomarker in the exhaled breath is determined from the measured rate of change in temperature;
    wherein:
    the biomarker is a ketone;
    the thermochemical reactant is selected from the group consisting of hydroxylamine hydrochloride and O-benzylhydroxylamine hydrochloride; and
    the sensitivity booster comprises a metal.

2. The device according to claim 1, wherein the sensitivity booster is at least one layer on the thermochemical reactant.

3. The device according to claim 1, wherein the sensitivity booster is dispersed in the thermochemical reactant.

4. The device according to claim 1, wherein the sensing element comprises a support element for supporting the thermochemical reactant.

5. The device according to claim 1, wherein the sensing element is mounted in a housing, the housing comprising an inlet for receiving the exhaled breath.

6. The device according to claim 5, wherein the sensing element is removably mounted in the housing.

7. The device according to claim 1, wherein the device is configured to receive a predetermined volume of the exhaled breath.

8. The device according to claim 1, further comprising a flow meter for measuring a flow rate of the exhaled breath into the device.

9. The device according to claim 1, wherein the biomarker is acetone.

10. The device according to claim 9, wherein the thermochemical reactant is hydroxylamine hydrochloride.

11. The device according to claim 9, wherein the sensitivity booster is aluminium.

12. The device according to claim 1, further comprising processing means for receiving data describing the measured rate of change in temperature and determining from the data the measure of the biomarker in the exhaled breath.

13. The device according to claim 12, wherein the processing means communicates a determined measure of the biomarker in the exhaled breath to the user interface.

14. The device according to claim 1, wherein the thermal sensor comprises a temperature dependant colour change material, and wherein the indicated measure of the biomarker in the exhaled breath is based on the colour of the material a predetermined period of time after the exhaled breath is introduced to the device.

15. The device according to claim 1, wherein the device is configured to receive the exhaled breath from a subject's mouth.

16. The device according to claim 1, wherein the device is configured to receive the exhaled breath from a subject's nose.

17. The device according to claim 1, further comprising a reference thermal sensor positioned to measure background temperatures in the device.

18. A method of monitoring a biomarker in an exhaled breath comprising:
    contacting the exhaled breath with a sensing element, the sensing element comprising:
        a thermochemical reactant that undergoes a thermochemical reaction with the biomarker, and
        a sensitivity booster in contact with the thermochemical reactant, wherein the sensitivity booster undergoes a second thermochemical reaction with a product of the reaction between the thermochemical reactant and the biomarker;
    measuring with a thermal sensor a rate of change in temperature caused by the thermochemical reaction; and
    determining from a measured rate of change in temperature a measure of the biomarker in the exhaled breath;
    wherein:
    the biomarker is a ketone;
    the thermochemical reactant is selected from the group consisting of hydroxylamine hydrochloride and O-benzylhydroxylamine hydrochloride; and the sensitivity booster comprises a metal.

* * * * *